(12) United States Patent
Ehmke et al.

(10) Patent No.: US 9,433,451 B2
(45) Date of Patent: Sep. 6, 2016

(54) HIP FIXATION SYSTEM WITH A COMPLIANT FIXATION ELEMENT

(71) Applicant: ACUMED LLC, Hillsboro, OR (US)

(72) Inventors: Larry W. Ehmke, Beaverton, OR (US); Steven P. Horst, Dayton, OR (US); Mark B. Sommers, Beaverton, OR (US); Brian R. Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 14/566,350

(22) Filed: Dec. 10, 2014

(65) Prior Publication Data

US 2015/0157371 A1 Jun. 11, 2015

Related U.S. Application Data

(63) Continuation-in-part of application No. 14/565,105, filed on Dec. 9, 2014, and a continuation-in-part of application No. 14/565,116, filed on Dec. 9, 2014.

(60) Provisional application No. 61/914,180, filed on Dec. 10, 2013, provisional application No. 61/913,593, filed on Dec. 9, 2013, provisional application No. 61/913,611, filed on Dec. 9, 2013.

(51) Int. Cl.
*A61B 17/74* (2006.01)

(52) U.S. Cl.
CPC ............ *A61B 17/746* (2013.01); *A61B 17/744* (2013.01)

(58) Field of Classification Search
CPC ......................... A61B 17/744; A61B 17/746
USPC ............ 606/62–68, 280, 281, 286, 300, 102
See application file for complete search history.

(56) References Cited

U.S. PATENT DOCUMENTS 2,699,774 A * 1/1955 Livingston ........... A61B 17/746
606/65
4,129,903 A 12/1978 Huggler
(Continued)

FOREIGN PATENT DOCUMENTS

WO 2008098728 A2 8/2008

OTHER PUBLICATIONS

Biomet Trauma, "VHS® Vari-Angle Hip System Surgical Technique" © 2008 Biomet, rev. Mar. 2008, 12 pages.
(Continued)

*Primary Examiner* — Pedro Philogene
*Assistant Examiner* — David C Comstock
(74) *Attorney, Agent, or Firm* — Kolisch Hartwell, P.C.

(57) ABSTRACT

System, including methods, devices, and kits, for hip fixation. The system may include a support member defining an aperture and including an intramedullary nail for a proximal femur or a plate member for a proximal femur. The system also may include a fixation element having a compliant region and configured to be received in the aperture of the support member such that the fixation element extends out of the support member from the aperture and into a head of the proximal femur and is slideable with respect to the support member along a long axis defined by the fixation element. The system further may include a set of stiffening inserts each insertable into the fixation element and configured to stiffen the compliant region differently from one another.

5 Claims, 10 Drawing Sheets

(56) References Cited

U.S. PATENT DOCUMENTS

| | | | |
|---|---|---|---|
| 4,399,813 A | 8/1983 | Barber | |
| 4,657,001 A | 4/1987 | Fixel | |
| 4,776,330 A | 10/1988 | Chapman et al. | |
| 4,959,064 A | 9/1990 | Engelhardt | |
| 5,032,125 A | 7/1991 | Durham et al. | |
| 5,041,116 A | 8/1991 | Wilson | |
| 5,098,434 A | 3/1992 | Serbousek | |
| 5,176,681 A | 1/1993 | Lawes et al. | |
| 5,578,035 A | 11/1996 | Lin | |
| 5,728,099 A | 3/1998 | Tellman et al. | |
| 5,743,912 A | 4/1998 | Lahille et al. | |
| 5,759,184 A | 6/1998 | Santangelo | |
| 6,106,528 A | 8/2000 | Durham et al. | |
| 6,238,126 B1 | 5/2001 | Dall | |
| 6,296,645 B1 | 10/2001 | Hover et al. | |
| 6,443,954 B1 | 9/2002 | Bramlet et al. | |
| 6,468,278 B1 | 10/2002 | Muckter | |
| 6,562,042 B2 | 5/2003 | Nelson | |
| 6,645,209 B2 | 11/2003 | Hall, IV et al. | |
| 6,648,889 B2 | 11/2003 | Bramlet et al. | |
| 6,695,844 B2 | 2/2004 | Bramlet et al. | |
| 6,783,530 B1 | 8/2004 | Levy | |
| 6,855,146 B2 | 2/2005 | Frigg et al. | |
| 7,041,104 B1 | 5/2006 | Cole et al. | |
| 7,135,023 B2 | 11/2006 | Watkins et al. | |
| 7,175,626 B2 | 2/2007 | Neff | |
| 7,503,919 B2 | 3/2009 | Shaw | |
| 7,569,055 B2 | 8/2009 | Zander et al. | |
| 7,591,819 B2 | 9/2009 | Zander et al. | |
| 7,763,023 B2 | 7/2010 | Gotfried | |
| 7,972,336 B2 | 7/2011 | James et al. | |
| 8,114,078 B2 | 2/2012 | Aschmann | |
| 8,137,348 B2 | 3/2012 | Gotfried | |
| 8,157,803 B1 | 4/2012 | Zirkle, Jr. et al. | |
| 8,158,802 B2 | 4/2012 | Lahm et al. | |
| 8,172,841 B2 | 5/2012 | Defossez | |
| 8,177,786 B2 | 5/2012 | Leyden et al. | |
| 8,241,287 B2 | 8/2012 | Prager et al. | |
| 8,252,059 B2 | 8/2012 | Overes et al. | |
| 8,287,540 B2 | 10/2012 | LeCronier et al. | |
| 8,398,636 B2 | 3/2013 | Simon et al. | |
| 8,414,582 B2 | 4/2013 | Overes et al. | |
| 8,617,227 B2 | 12/2013 | Sucec et al. | |
| 8,790,343 B2 | 7/2014 | McClellan et al. | |
| 9,254,153 B2 | 2/2016 | Simon et al. | |
| 2002/0007185 A1 | 1/2002 | Aghion | |
| 2002/0032445 A1 | 3/2002 | Fujiwara | |
| 2002/0173792 A1 | 11/2002 | Severns et al. | |
| 2003/0074000 A1 | 4/2003 | Roth et al. | |
| 2004/0260290 A1 | 12/2004 | Zander et al. | |
| 2005/0010224 A1 | 1/2005 | Watkins et al. | |
| 2005/0055024 A1 | 3/2005 | James et al. | |
| 2005/0143739 A1 | 6/2005 | Shinjo et al. | |
| 2005/0203510 A1 | 9/2005 | Sohngen | |
| 2006/0095039 A1 | 5/2006 | Mutchler | |
| 2006/0149248 A1 | 7/2006 | Schlienger et al. | |
| 2006/0155281 A1 | 7/2006 | Kaup et al. | |
| 2006/0200160 A1 | 9/2006 | Border et al. | |
| 2006/0241604 A1 | 10/2006 | Frigg et al. | |
| 2006/0241606 A1 | 10/2006 | Vachtenberg et al. | |
| 2007/0100343 A1 | 5/2007 | Cole et al. | |
| 2007/0219636 A1* | 9/2007 | Thakkar | A61B 17/1721 623/18.11 |
| 2007/0270847 A1 | 11/2007 | Shaw | |
| 2008/0140077 A1 | 6/2008 | Kebaish | |
| 2008/0177291 A1 | 7/2008 | Jensen et al. | |
| 2008/0183170 A1* | 7/2008 | Metzinger | A61B 17/7208 606/62 |
| 2008/0255559 A1 | 10/2008 | Leyden et al. | |
| 2008/0269752 A1 | 10/2008 | Simon et al. | |
| 2008/0281326 A1 | 11/2008 | Watanabe et al. | |
| 2009/0048600 A1 | 2/2009 | Matityahu et al. | |
| 2009/0048606 A1 | 2/2009 | Tipirneni et al. | |
| 2009/0088752 A1 | 4/2009 | Metzinger et al. | |
| 2009/0248025 A1 | 10/2009 | Haidukewych et al. | |
| 2009/0326534 A1 | 12/2009 | Yamazaki et al. | |
| 2010/0121327 A1 | 5/2010 | Velikov | |
| 2010/0179549 A1 | 7/2010 | Keller et al. | |
| 2010/0179551 A1 | 7/2010 | Keller et al. | |
| 2010/0249781 A1 | 9/2010 | Haidukewych et al. | |
| 2010/0249852 A1 | 9/2010 | Brumfield et al. | |
| 2010/0268285 A1 | 10/2010 | Tipirneni et al. | |
| 2010/0331843 A1 | 12/2010 | Grusin | |
| 2011/0196370 A1 | 8/2011 | Mikhail | |
| 2011/0295255 A1 | 12/2011 | Roberts et al. | |
| 2012/0109128 A1 | 5/2012 | Frigg | |
| 2012/0130370 A1 | 5/2012 | Kinmon | |
| 2012/0136356 A1 | 5/2012 | Doherty et al. | |
| 2012/0310289 A1 | 12/2012 | Bottlang et al. | |
| 2013/0041414 A1 | 2/2013 | Epperly et al. | |
| 2013/0204304 A1 | 8/2013 | Bottlang et al. | |
| 2014/0052132 A1 | 2/2014 | Matityahu et al. | |
| 2014/0058392 A1 | 2/2014 | Mueckter et al. | |
| 2014/0094802 A1 | 4/2014 | Simon et al. | |
| 2014/0135769 A1 | 5/2014 | Ziran | |
| 2014/0214035 A1 | 7/2014 | Simon | |
| 2014/0214098 A1 | 7/2014 | Probe et al. | |
| 2014/0330274 A1 | 11/2014 | Matityahu et al. | |
| 2015/0250507 A1 | 9/2015 | Harrison et al. | |
| 2016/0051295 A1 | 2/2016 | Nakamura et al. | |

OTHER PUBLICATIONS

Kwok Sui Leung, M.D. et al., "Gamma3 Trochanteric Nail 180" Operative Technique brochure, Stryker © 2011.

Amir Matityahu et al., "The Variable Angle Hip Fracture Nail Relative to the Gamma 3: A Finite Element Analysis Illustrating the Same Stiffness and Fatigue Characteristics", Hindawi Publishing Corporation, Advances in Orthopedics, vol. 2013, Article ID 143801, © 2013, 11 pages.

Blaine R. Copenheaver, Authorized Officer, U.S. Patent and Trademark Office, "International Search Report" in connection with related PCT Patent Application No. PCT/US2014/069575, dated Mar. 4, 2015, 2 pages.

Blaine R. Copenheaver, Authorized Officer, U.S. Patent and Trademark Office, "Written Opinion of the International Searching Authority" in connection with related PCT Patent Application No. PCT/US2014/069575, dated Mar. 4, 2015, 6 pages.

\* cited by examiner

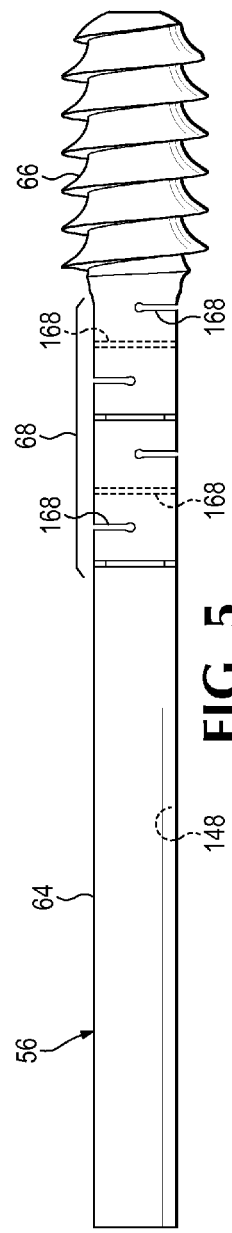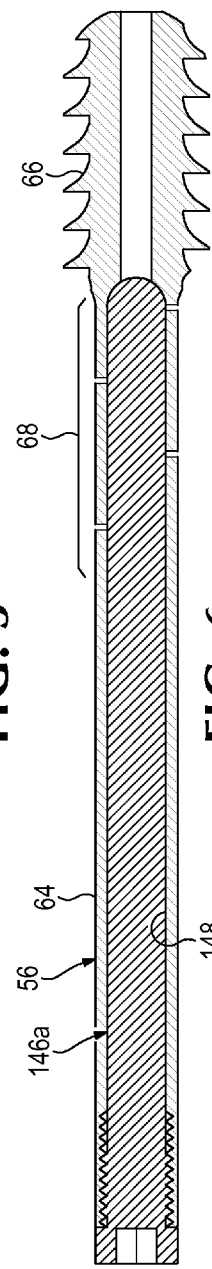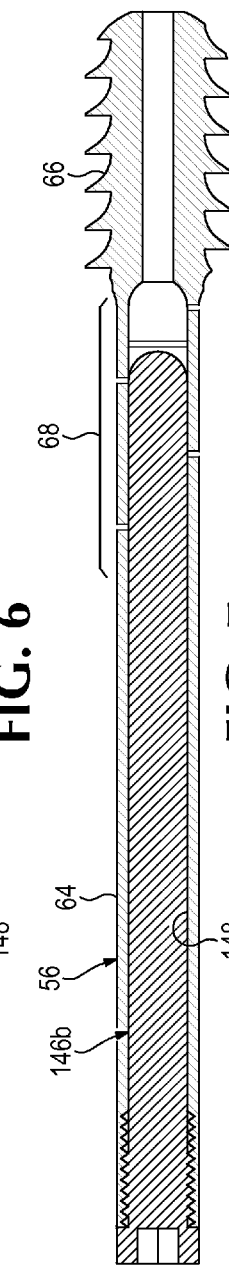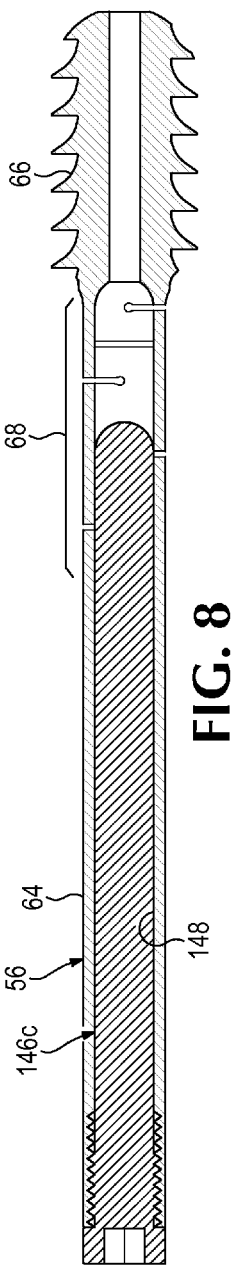

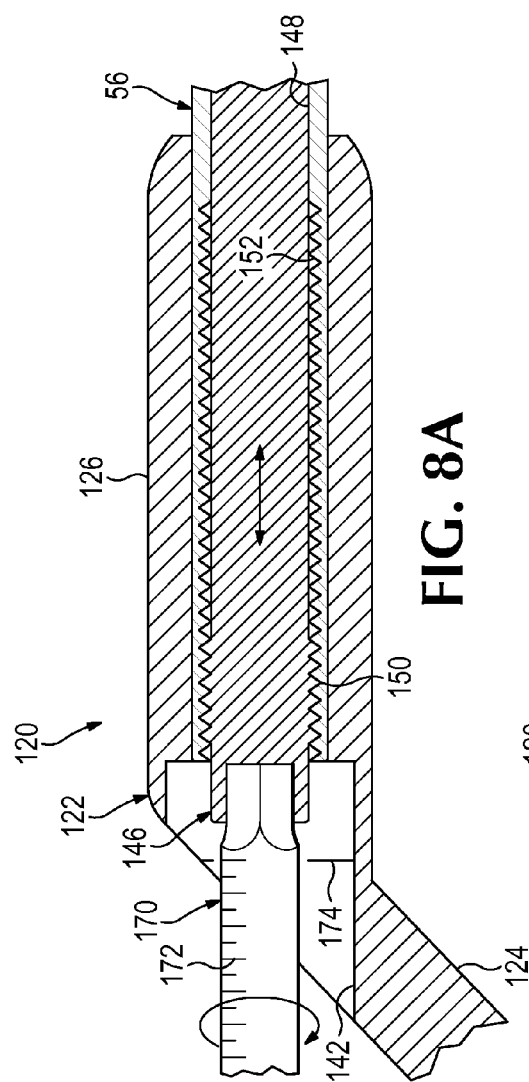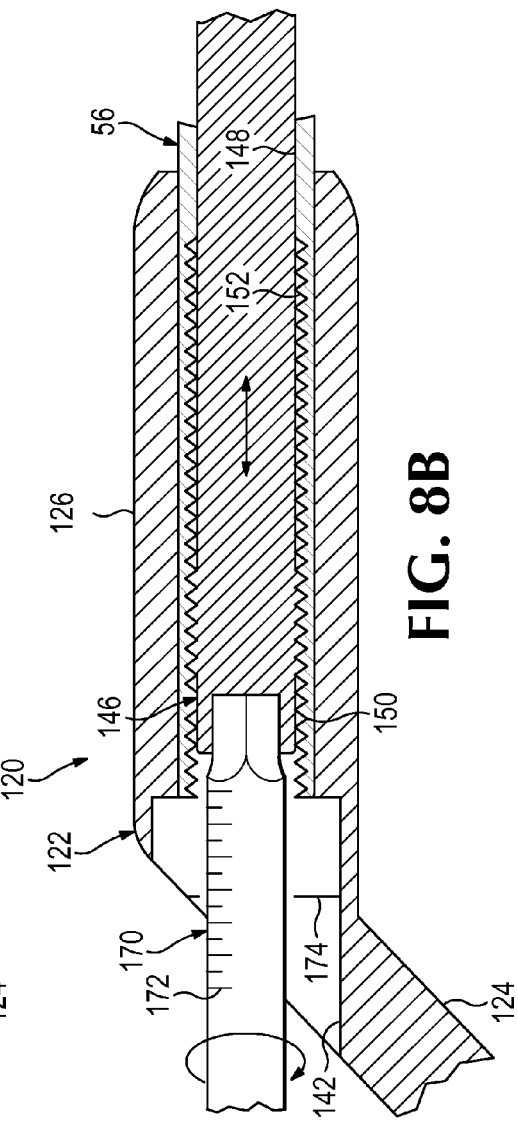

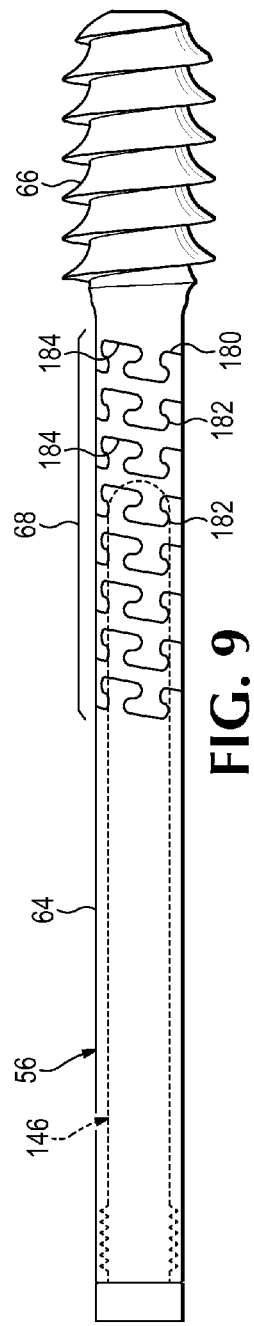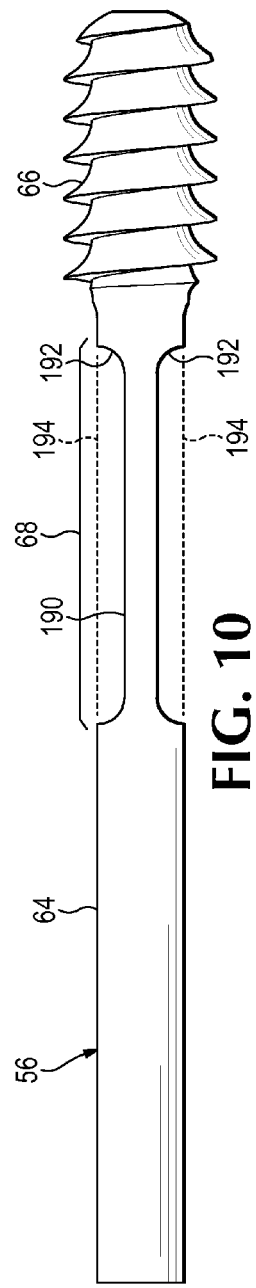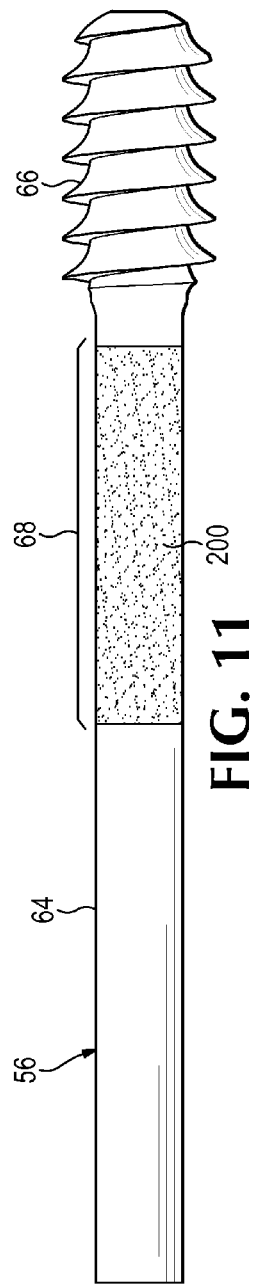

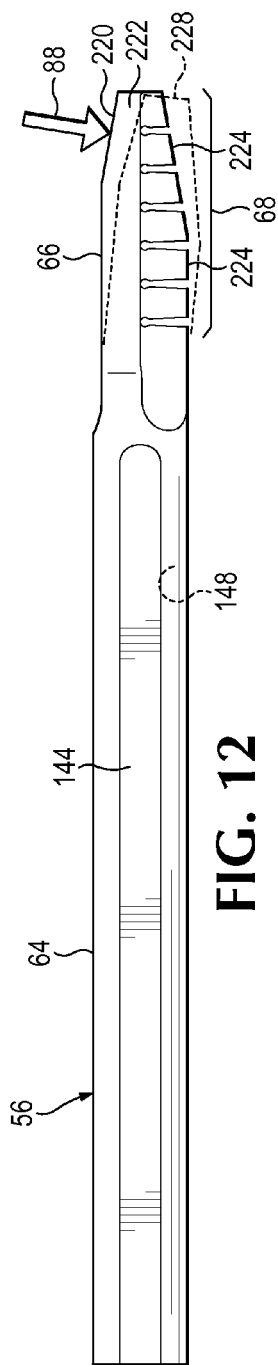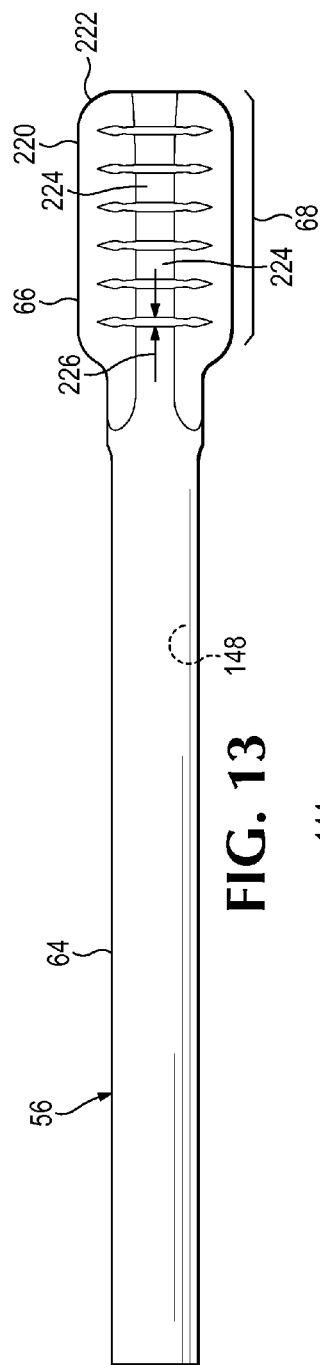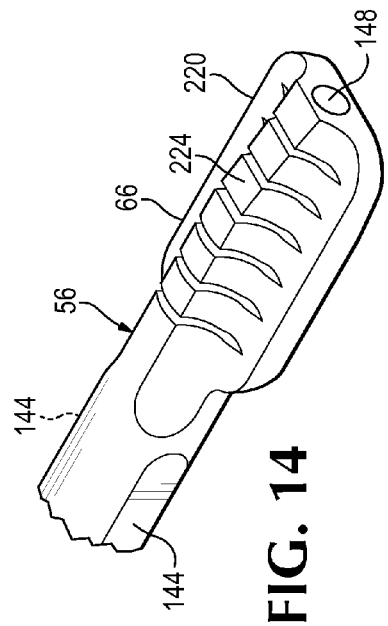

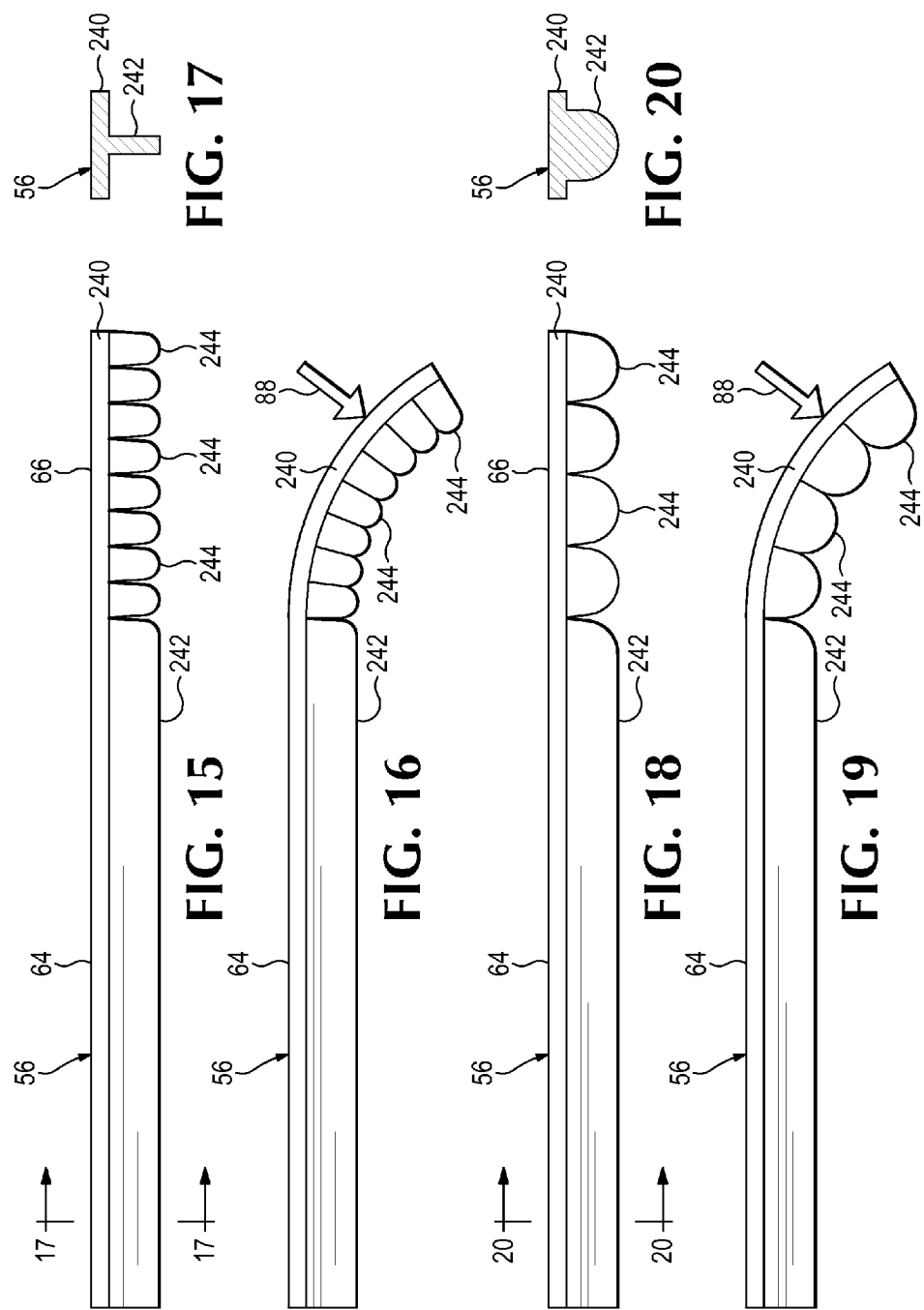

HIP FIXATION SYSTEM WITH A COMPLIANT FIXATION ELEMENT

CROSS-REFERENCES TO PRIORITY APPLICATIONS

This application is based upon and claims the benefit under 35 U.S.C. §119(e) of U.S. Provisional Patent Application Ser. No. 61/914,180, filed Dec. 10, 2013, and is a continuation-in-part of U.S. patent application Ser. No. 14/565,105, filed Dec. 9, 2014; and U.S. patent application Ser. No. 14/565,116, filed Dec. 9, 2014. The Ser. No. 14/565,105 application, in turn, claims priority from U.S. Provisional Patent Application Ser. No. 61/913,593, filed Dec. 9, 2013. The Ser. No. 14/565,116 application, in turn, claims priority from U.S. Provisional Patent Application Ser. No. 61/913,611, filed Dec. 9, 2013. Each of these priority applications is incorporated herein by reference in its entirety for all purposes

INTRODUCTION

The hip joint is a synovial joint formed by articulation of the head of the proximal femur and the acetabulum of the pelvis. The hip joint(s) supports the weight of the body when a person is standing, walking, or running, among others.

Trauma to the femur can fracture the proximal femur near the hip joint. Depending on the position and severity of fracture, the femoral head may be replaced with a prosthesis, or the bone may be stabilized with an implanted fixation device to hold the femoral head in position while the femur heals.

A nail-based fixation device involving an intramedullary nail and a screw is commonly utilized for fixation. The nail is placed axially into the proximal femur from a proximal end thereof. Then, the screw is inserted obliquely into the proximal femur from a lateral side thereof, through the nail and the femoral neck, and into the femoral head. The screw may be placed at an angle of about 125 degrees with respect to the nail, to account for the angle between the femoral head/neck and the femoral shaft. The screw and the nail both generally span the fracture. Accordingly, the screw can transfer the load from the femoral head to the nail, which can stabilize the fractured femur more effectively and improve healing.

A plate-based fixation device involving a side plate and a sliding screw is commonly utilized for fixation. The side plate has a barrel portion for receiving a portion of the screw. The screw is inserted obliquely into the proximal femur from a lateral side thereof, such that the screw extends through the femoral neck and into the femoral head, and generally bridges at least one fracture. The screw may, for example, be placed at an angle about 135 degrees with respect to the femur, to account for the angle between the femoral head/neck and the femoral shaft. The side plate then is affixed to the lateral side of the proximal femur, with the barrel extending into the proximal femur and surrounding a trailing portion of the screw.

The screw may not be fixed with respect to the nail or with respect to the barrel of the side plate. Instead, the screw may be permitted to slide parallel to its long axis in the nail or barrel. More particularly, the screw may be allowed to migrate laterally (anatomically) after installation, for dynamic compression of the fracture, which can encourage and improve fracture healing.

The ability of the screw to migrate can improve performance dramatically. However, the fixation device does not always provide a successful outcome. In some cases, the femoral head is damaged by cut-out, where migration of the femoral head relative to the screw causes the screw to project through the articular surface of the femoral head, and/or to split the femoral head.

An improved nail-based or plate-based hip fixation system is needed.

SUMMARY

The present disclosure provides a system, including methods, devices, and kits, for hip fixation. The system may include a support member defining an aperture and including an intramedullary nail or a plate member for a proximal femur. The system also may include a fixation element having a reversibly deformable compliant region and configured to be received in the aperture of the support member such that the fixation element extends out of the support member from the aperture and into a head of the proximal femur and is slideable with respect to the support member parallel to a long axis defined by the fixation element. The system further may include a stiffening insert that is insertable into the fixation element to reduce a deformability of the compliant region.

BRIEF DESCRIPTION OF THE DRAWINGS

FIG. 5 is a side view of a fixation element for the nail-based system of FIG. 1 or the plate-based system of FIG. 2, in accordance with aspects of the present disclosure.

FIGS. 6-8 are longitudinal sectional views of the fixation element of FIG. 5 assembled with an exemplary set of stiffening inserts configured to stiffen a compliant region of the fixation element differently from one another, in accordance with aspects of the present disclosure.

FIG. 8A is a fragmentary sectional view of yet another modified version of the plate-based fixation system of FIG. 2, taken as in FIG. 4 through a center plane of the system in the presence of a driver having a depth gauge, in accordance with aspects of the present disclosure.

FIG. 8B a view of the fixation system and driver of FIG. 8A, taken after axial advancement of the stiffening insert to reduce the flexibility of the fixation element at the compliant region thereof.

FIG. 9 is a side view of another exemplary fixation element for the nail-based system of FIG. 1 or the plate-based system of FIG. 2, with the fixation element defining a sinuous helical slit that forms a compliant region of the fixation element, in accordance with aspects of the present disclosure.

FIG. 10 is a side view of still another exemplary fixation element for the nail-based system of FIG. 1 or the plate-based system of FIG. 2, with the fixation element having a neck region that forms a compliant region of the fixation element, in accordance with aspects of the present disclosure.

FIG. 11 is a side view of still another exemplary fixation element for the nail-based system of FIG. 1 or the plate-based system of FIG. 2, with the fixation element having a compliant region of different composition than other longitudinal regions of the fixation element, in accordance with aspects of the present disclosure.

FIG. 12 is a side view of yet another exemplary fixation element for the nail-based system of FIG. 1 or the plate-based system of FIG. 2, with the fixation element being a paddle member including a compliant blade to anchor the fixation element in the head of the proximal femur, in accordance with aspects of the present disclosure.

FIG. 13 is another view of the fixation element of FIG. 12, taken along a viewing axis that is orthogonal to the viewing axis of FIG. 12.

FIG. 14 is a fragmentary isometric view of the fixation element of FIG. 12, taken generally around the compliant blade.

FIG. 15 is a side view of still yet another exemplary fixation element for the nail-based system of FIG. 1 or the plate-based system of FIG. 2, with the fixation element including a compliant blade to anchor the fixation element in the head of the proximal femur, in accordance with aspects of the present disclosure.

FIG. 16 is another side view of the fixation element of FIG. 15, taken with the fixation element loaded with a downward force that has deformed the compliant blade to a deformation limit.

FIG. 17 is a sectional view of the fixation element of FIG. 15, taken generally along line 17-17 of FIG. 15.

FIG. 18 is a side view of yet still another exemplary fixation element for the nail-based system of FIG. 1 or the plate-based system of FIG. 2, with the fixation element structured generally as in FIG. 15 to form a compliant blade but with wider teeth than in FIG. 15, in accordance with aspects of the present disclosure.

FIG. 19 is another side view of the fixation element of FIG. 19, taken with the fixation element loaded with a downward force that has deformed the compliant blade to a deformation limit.

FIG. 20 is a sectional view of the fixation element of FIG. 18, taken generally along line 20-20 of FIG. 18.

DETAILED DESCRIPTION

The present disclosure provides a system, including methods, devices, and kits, for hip fixation. The system may include a support member defining an aperture and including an intramedullary nail or a plate member for a proximal femur. The system also may include a fixation element having a reversibly deformable compliant region and configured to be received in the aperture of the support member such that the fixation element extends out of the support member from the aperture and into a head of the proximal femur and is slideable with respect to the support member parallel to a long axis defined by the fixation element. The system further may include a stiffening insert that is insertable at least partially into the fixation element to reduce a deformability of the compliant region.

The hip fixation system of the present disclosure may have a reduced stiffness (greater compliance), to reduce the peak loads created at the implant-bone interface (in the femoral head), thereby reducing the propensity for microcrack formation, which can ultimately lead to cut-out of the implant through the femoral head. Accordingly, the hip fixation system may have various advantages over existing hip fixation systems including a lower incidence of cut-out through the femoral head, improved patient comfort, better force dampening, less swarf created through wear, and/or the like.

Further aspects of the present disclosure are described in the following sections: (I) overview of compliant hip fixation systems, (II) methods of hip fixation, (III) composition of system components, (IV) kits, and (V) examples.

I. OVERVIEW OF COMPLIANT HIP FIXATION SYSTEMS

This section describes exemplary compliant hip fixation systems having a deformable fixation element and an optional stiffening insert that reduces the deformability of a compliant region of the fixation element, with each system also optionally having a compliant interface operatively positioned between the fixation element and a nail or plate member; see FIGS. 1-4, 4A, 4B, 5-8, 8A, and 8B.

Figure 1:
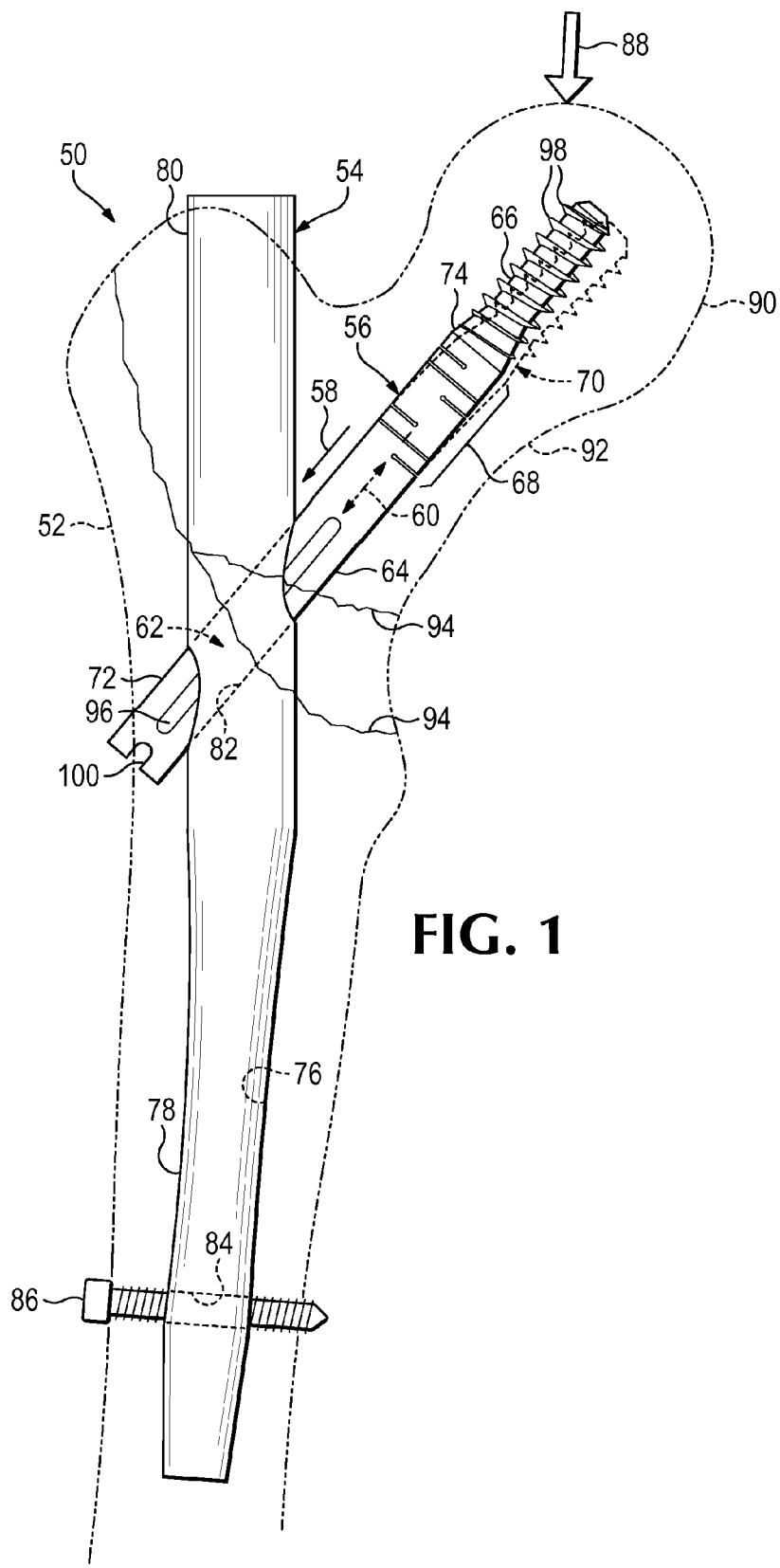
FIG. 1 is a front view of an exemplary nail-based compliant hip fixation system installed in a fractured proximal femur and including an intramedullary nail and a deformable, axially slideable fixation element extending obliquely through the nail and into a head of the proximal femur, with deformation of the fixation element shown in phantom outline, in accordance with aspects of the present disclosure.

FIG. 1 shows a front view of an exemplary nail-based hip fixation system 50 installed in a fractured proximal femur 52. System 50 (interchangeably termed an implant or a device) may include an intramedullary nail 54 (interchangeable termed a support member) intersected by a deformable fixation element 56 (interchangeably called a fastener). Fixation element 56 may be slideable, indicated by a motion arrow at 58, relative to the nail on an axis 60. The axis may be coaxial to the central long axis of the fixation element. In some embodiments, axis 60 may be movable via deformation of a compliant interface 62 located in nail 54, to change an angular orientation of the fixation element with respect to the nail. Exemplary compliant members for the compliant interface are described in the patent applications listed above under Cross-References to Priority applications, particularly U.S. patent application Ser. No. 14/565,105, filed Dec. 9, 2014, and U.S. patent application Ser. No. 14/565,116, filed Dec. 9, 2014, which are incorporated herein by reference.

Fixation element 56 includes a shaft 64 and a bone-securing portion 66 projecting from an inner end (a leading end) of the shaft. The fixation element also has a compliant region 68 that renders the fixation element reversibly deformable. Compliant region 68 may be part of shaft 64, bone-securing portion 66, or both. The compliant region may allow reversible movement of portions of the fixation element relative to one another. For example, the compliant region may impart flexibility to the fixation element to allow the fixation element to deform from a linear configuration to a bent configuration, indicated in phantom outline at 70. More particularly, a trailing region 72 and a leading region 74 (including bone-securing portion 66) of the fixation element, arranged longitudinally with respect to one another along the fixation element, may move relative to one another, such as out of coaxial alignment with one another, which may change the central longitudinal path of the fixation element from linear to nonlinear. In some embodiments, the fixation element may be deformable within the bone-securing portion (see Examples 2 and 3 of Section V).

Fixation element 56 may retain the ability to slide along its long axis as compliant region 68 (and/or compliant interface 62) deforms. In some embodiments, the fixation element may not be slideable in the nail after the fixation system is fully installed in the femur. In some embodiments, the fixation element may be slideable in both directions parallel to the long axis of the fixation element. In some embodiments, the fixation element may be slideable laterally and not medially along the long axis of the fixation element.

Nail 54 may be configured to be placed into a medullary canal 76 of proximal femur 52 from a proximal end thereof. The end of the nail may be flush, recessed, or protruding after placement into the proximal femur. The nail may have a leading region 78 projecting from a trailing region 80. The leading region may have a smaller average diameter than the trailing region and may be described as a stem or shaft, and the trailing region as a head. The nail may taper toward the leading region and/or the leading boundary of the nail. The nail may be linear such that leading and trailing regions 78, 80 are coaxial. Alternatively, the nail may have a longitudinal bend, as shown, such that the leading and trailing regions are angularly offset from one another by at least about 1, 2, 4, or 6 degrees, among others.

The nail may define one or more transverse apertures 82, 84 that extend transversely (orthogonally or obliquely) through the nail, such as between opposite side wall regions of the nail. Each aperture may be a locking (e.g., threaded) or nonlocking aperture. Proximal aperture 82 may be defined by trailing region 80 of the nail. The proximal aperture may be sized to receive and surround a region of fixation element 56, with the fixation element extending through the aperture.

The nail also may define one or more distal transverse apertures 84 to receive at least one other fastener, such as a bone screw 86, that attaches leading region 74 of the nail to a shaft region of the femur. The nail further may define an axial bore that extends into the nail from the nail's trailing boundary. The axial bore may extend along any suitable portion of the length of the nail, such as only into the trailing region, through the trailing region and into the leading region but not completely through the nail, or through the entire length of the nail. In some embodiments, the nail may define two or more proximal apertures to receive two or more proximal fixation elements 56.

Proximal aperture 82 (and/or fixation element 56) may extend through nail 54 transversely, at an oblique angle relative to the nail, such as at an obtuse angle of greater than about 110 degrees or about 110-150, 120-140, or 120-130 degrees, among others. The proximal aperture may or may not be cylindrical and may or may not vary in diameter along the aperture.

The wall of the proximal aperture may or may not be configured to contact the fixation element. For example, at least one bearing member, such as a sleeve (interchangeably termed a bushing), may be positioned and/or mounted in the aperture. The sleeve may contact the fixation element while permitting the fixation element to slide in the nail. The sleeve may maintain separation between nail 54 and fixation element 56. The sleeve may define a channel that is slightly larger than the diameter of the shaft of the fixation element, to allow the fixation element to slide in the channel without any substantial change in the angular orientation of the fixation element with respect to the sleeve.

Compliant region 68 of fixation element 56 may have any suitable properties. The compliant region alternatively may be described as a deformable region of the fixation element. A downward force or load 88 applied to the end of fixation element 56 via bone, such as when a subject (the implant recipient) is standing or walking, applies a torque to fixation element 56. The torque may cause deformation of compliant region 68 and an accompanying change in the relative positions of regions of the fixation element. Deformation of the compliant region may absorb some of the load applied to the hip joint and may help to govern and cushion load transfer during use of the hip joint (such as when walking). At least a region of bone-securing portion 66 may change its angular orientation in a varus direction, as shown, in response to load 88. The attached femoral head 90 may move with the fixation element, producing varus travel of the femoral head, which may reduce the tendency of the fixation element to move relative to the femoral head.

Deformation of fixation element 56 may be dynamic as the subject moves. For example, this deformation may be cyclical when the subject walks. The fixation element may deform when load 88 is applied (i.e., when the associated femur is bearing the weight of the subject) and may return to an undeformed (or less deformed) configuration when load 88 is removed (e.g., when the contralateral femur is bearing the weight of the subject).

Compliant region 68 may permit the angular orientation of at least a region of bone-securing portion 66 (and/or leading region 74) to change with respect to shaft 64 (and/or trailing region 72) by any suitable amount from a relatively neutral or unloaded ("home") configuration during normal use, such as less than about 5 or 2 degrees, and/or at least about 0.2, 0.5, or 1 degree, among others. At least a region of bone-securing portion 66 (and/or leading region 74) may have a maximum range of motion produced by deformation of the fixation element, from the neutral or unloaded configuration during normal use, of less than about 5 mm or 2 mm, or greater than about 0.5 mm or 1 mm, among others.

The compliant region is resilient (interchangeably termed elastic), meaning that the compliant region is capable of recovering its previous shape (and/or size) after being deformed (i.e., after a deforming force/load is removed).

The resiliency of the compliant region stores energy and then uses the stored energy to urge the fixation element back toward a neutral/unloaded configuration when the load is reduced or removed. The compliant region may be formed integrally with shaft 64 and bone-securing portion 66 of fixation element 56, or at least part of the compliant region may be formed separately from the shaft and/or bone-securing portion. In some embodiments, the compliant region may be described as a spring. The compliant region can act as a mechanical damper, which may absorb energy to function as a cushion, particularly to absorb sudden impacts produced by standing up, walking, running, etc.

In some embodiments, the compliant region may provide non-linear load resistance/absorption. For example, as the compliant region is deformed, further deformation may be progressively more difficult and the load needed for further deformation may increase non-linearly. The compliant region may be formed of a single material or may be a composite of two or more materials, such as metal and polymer, to provide optimal dampening.

Compliant region 68 may have any suitable location and structure. The compliant region may be at least partially contained by nail 54 (or a barrel portion of a plate member (see below)) and thus may be disposed at least partially or completely inside the nail (or the barrel portion). Alternatively, the compliant region may be located at least partially or completely outside nail 54 (or the barrel portion of the plate member).

Compliant region 68 may provide radially uniform or radially nonuniform resistance to deformation of fixation element 56. In some embodiments, the compliant region may be configured to constrain relative motion within the fixation element to one plane of a set of three mutually orthogonal planes (such as a plane defined by the long axes of nail 54 (or a mounting portion of a plate member) and fixation element 56). In some embodiments, the compliant region may provide differential resistance to angular motion of a portion of the fixation element in opposite rotational directions in a plane, or may offer an equal resistance in both rotational directions. In some embodiments, the compliant region may permit motion of the fixation element in a first plane (such as a frontal plane) and in a second plane orthogonal to the first plane (e.g., to allow posterior and/or anterior motion of the fixation element). The compliant region may provide the same or different resistance to motion in the two planes, such as a greater (or lesser) resistance to motion in the first plane relative to the second plane.

Fixation element 56 may be configured to be disposed partially and slideably in nail 54 and to extend out the medial side of the nail, through femoral neck 92 and into femoral head 90, for anchorage therein. The fixation element and/or nail 54 may span at least one fracture 94.

Shaft 64 of fixation element 56 may have any suitable structure. The shaft may be a single piece, or two or more pieces, which may be assembled inside or outside the femur. The shaft may be at least generally cylindrical. The shaft may be shaped to prevent the fixation element from turning about the fixation element's long axis after the shaft is disposed in the nail. For example, the shaft may have one or more flats, grooves 96, and/or ridges, among others, extending along the shaft Grooves 96 (or ridges) of the fixation element may be engaged by an anti-rotation element, such as a set screw, connected to nail 54 and configured to prevent the fixation element from turning about its long axis. The set screw may be in threaded engagement with the nail and advanceable axially in the nail such that a leading end region of the set screw projects into one of grooves 96 of fixation element 56. The set screw may permit the fixation element to slide along its long axis both laterally and medially, or may restrict sliding medially (or both medially and laterally).

Bone-securing portion 66 forms one or more anchoring features to anchor the fixation element in the femoral head. In the depicted embodiment, bone-securing portion 66 defines an external thread 98 that attaches the bone-securing portion to femoral head 90. Accordingly, the fixation element may be a screw. In other embodiments, bone-securing portion 66 may define one or more blades, flanges, spikes, deployable talons, etc., or any combination thereof, among others, to provide anchorage in the femoral head.

Fixation element 56 may have any other suitable structure. The fixation element may be configured to apply compression to the femur, such as across at least one fracture 94 spanned by fixation element 56 and/or nail 54. The fixation element may define an internal thread for attachment to a compression screw and/or a driver, and/or an axial bore extending into and/or through the fixation element. The fixation element also may define an internal and/or external driver-engagement structure 100 for engagement by a driver that turns or otherwise urges the fixation element into bone. The driver-engagement structure may, for example, be at least one slot, a socket (e.g., a hexagonal socket), external flats (e.g., a hexagonal, faceted perimeter), etc.

Figure 2:
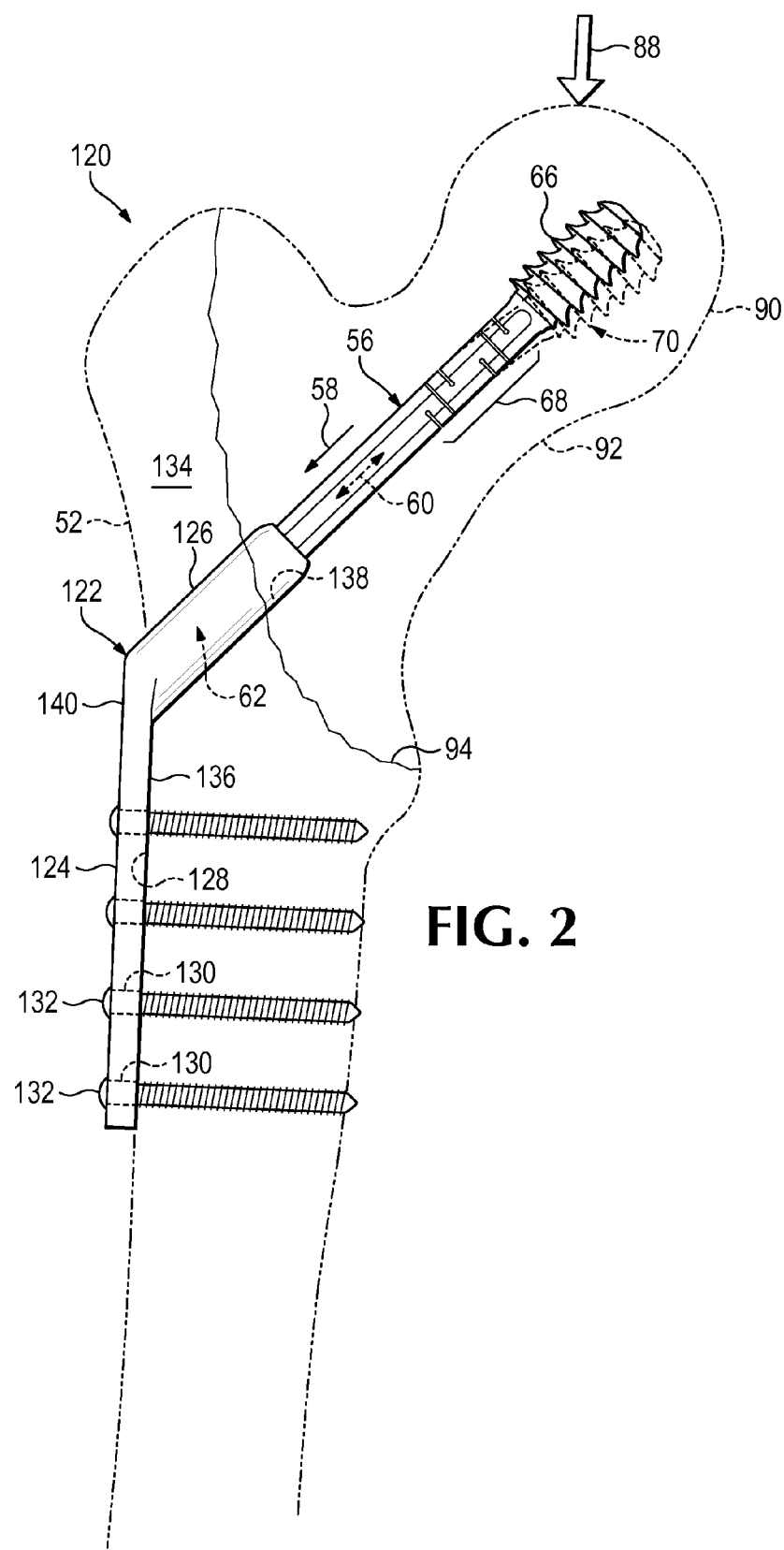
FIG. 2 is a front view of an exemplary plate-based compliant hip fixation system installed in a fractured proximal femur and including a side plate (a plate member) and a deformable, axially slideable fixation element that extends out of a barrel portion of the side plate and into a head of the proximal femur, with deformation of the fixation element shown in phantom outline, in accordance with aspects of the present disclosure.
Figure 3:
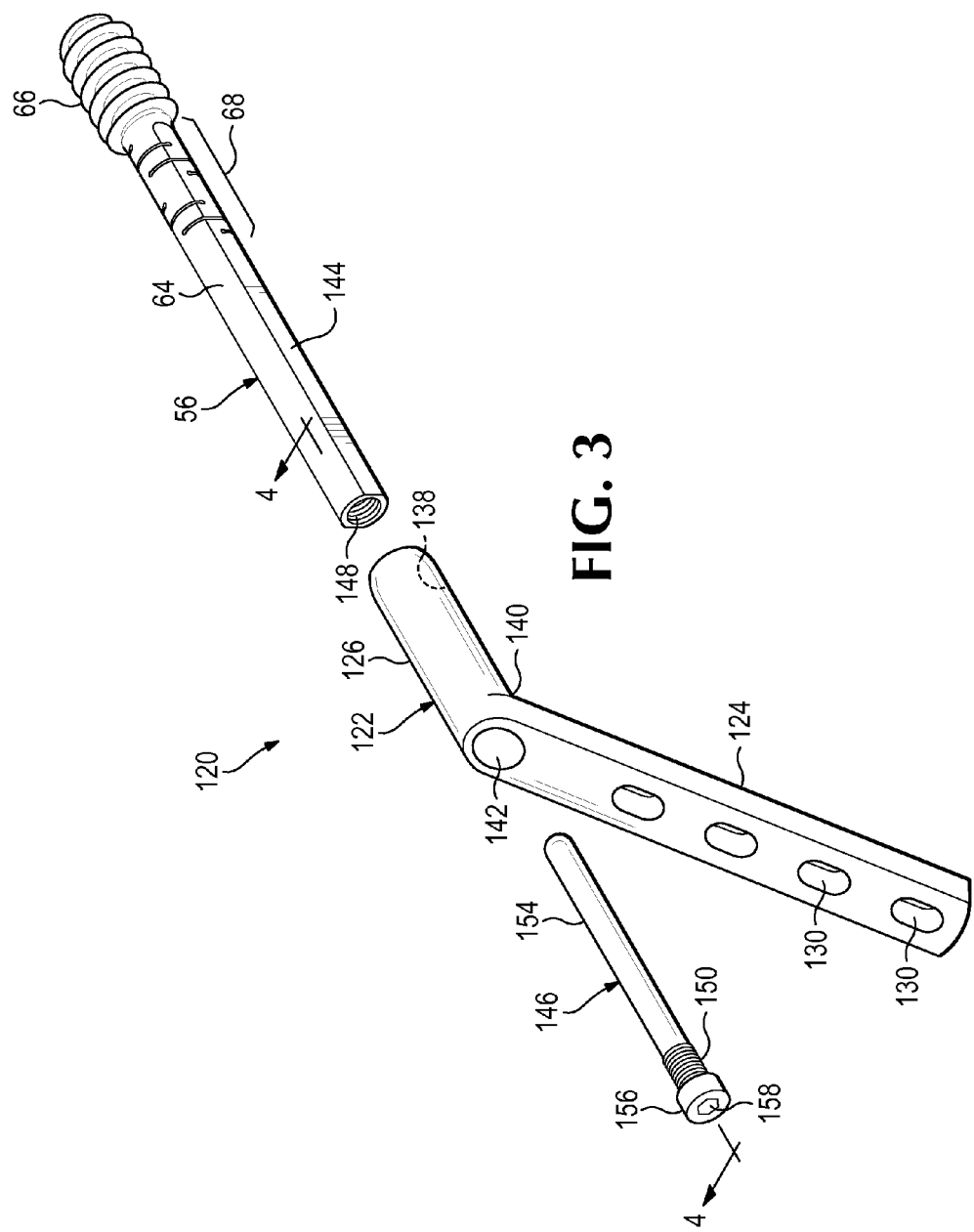
FIG. 3 is an exploded isometric view of selected aspects of the plate-based system of FIG. 2 taken in the absence of the proximal femur and four bone screws.
Figure 4:
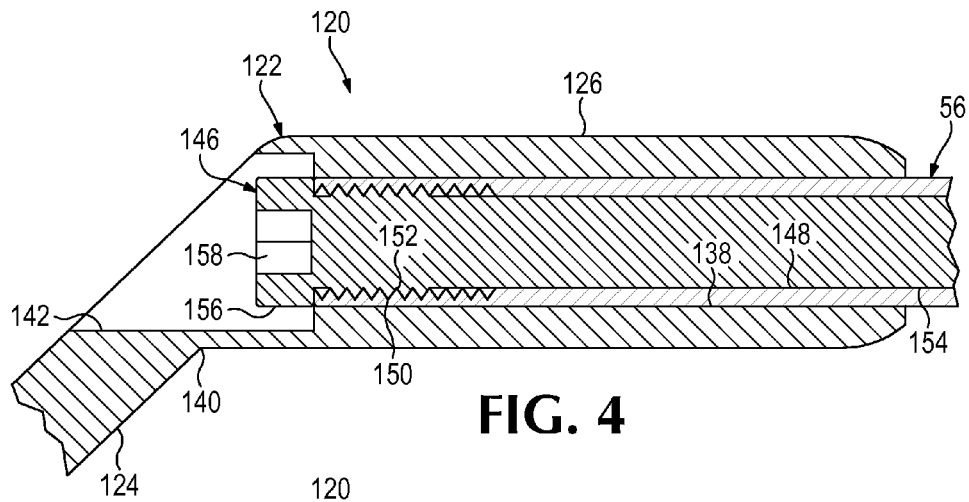
FIG. 4 is a fragmentary sectional view of the plate-based system of FIG. 2, taken generally along line 4-4 of FIG. 3 through a center plane of the system and showing the fixation element extending along the barrel portion of the side plate and assembled with a stiffening insert.

FIGS. 2-4 show respective front, exploded, and sectional views of an exemplary plate-based compliant hip fixation system 120 installed in a fractured femur 52 (FIG. 2) or in the absence of bone (FIGS. 3 and 4). System 120 (interchangeably termed an implant or a device) may include a plate member 122 and a deformable fixation element 56 (also see FIG. 1 and Section V). Plate member 122 may include a mounting portion 124 and a barrel portion 126. Plate member 122 interchangeably may be termed a support member including a plate portion (mounting portion 124) and barrel portion 126.

Plate-based system 120 and fixation element 56 may have any suitable combination of the elements and features described above for nail-based system 50. For example, system 120 may have a compliant interface 62 disposed at least partially in barrel portion 126 and/or permitting a reversible change in the angular orientation of fixation element 56 in response to a load 88. Alternatively, or in addition, fixation element 56 of system 120 may have a compliant region 68 as described above. Fixation element 56 may be slideable, indicated at 58, along axis 60, as described above for system 50. Furthermore, the angular orientation of the fixation element may vary as compliant interface 62, if present, deforms.

Mounting portion 124 may be configured to be positioned at least predominantly or exclusively outside femur 52. The mounting portion may be placed on and attached to a lateral cortex 128 of the femur, with a long axis of the mounting portion extending longitudinally along the femur (see FIG. 2). The mounting portion may define at least one or a plurality of apertures 130 for receiving fasteners, such as bone screws 132, that secure the mounting portion to the proximal femur. Each aperture 130 may be arranged outward of only one side of fixation element 56 and/or barrel portion 126, as shown, such that each aperture is positioned inferiorly along the femur with respect to the barrel portion after the system has been fully installed. Alternatively, apertures 130 may bracket the long axis of the fixation element and/or barrel portion, such that one or more apertures 130 are superior along the femur with respect to a junction where the barrel portion meets the mounting portion after the system has been fully installed. Each aperture 130 may or may not have an internal thread for attaching a fastener, such as a bone screw 132, to the mounting portion. Each fastener placed into bone from an aperture 130 may, for example, engage the femur unicortically, as shown in FIG. 2, or bicortically, among others.

Barrel portion 126 may be configured to be positioned at least partially or at least predominantly or substantially exclusively inside the femur. Barrel portion 126 may be configured to extend into a lateral region 134 of the femur (see FIG. 2). The barrel portion may be formed integrally with (or separately from) mounting portion 124. Accordingly, the barrel portion may or may not be removable from the mounting portion and may or may not have a fixed orientation with respect to the mounting portion. The barrel portion may be flexibly or rigidly (e.g., integrally) connected to the mounting portion. The barrel portion may project from the mounting portion, such as from a bone-facing surface 136 thereof, at an obtuse angle, such as at an angle of greater than about 110 degrees or about 120-150, 125-145, or 130-140 degrees, among others. The barrel portion may be rigid or flexible. In some embodiments, the barrel portion defines one or more slots or other openings that render the barrel portion flexible, to allow the fixation element to change its angular orientation.

The barrel portion may have any suitable external shape. The outside diameter of the barrel portion may be constant or may vary along the barrel portion. For example, the barrel portion may be round in cross section and the external shape may be cylindrical, conical, spherical, or a combination thereof, among others.

Plate member 122 may define an aperture, such as a channel 138, for receiving and surrounding a portion of fixation element 56 (see FIGS. 2-4). The channel may extend through plate member 122, and particularly through barrel portion 126. The channel has an outer end and an inner end. The outer end of the channel may be described as being defined by a junction region 140 of plate member 122, which may be formed by mounting portion 124 and/or barrel portion 126.

Channel 138 may have any suitable shape. The channel may or may not vary in diameter. If the diameter varies, this variation may be a taper or stepwise, or both, among others. In some embodiments, the channel may widen at its outer end, which may form a counterbore 142 (see FIGS. 3 and 4). In some embodiments, the channel may widen and then narrow at one or more positions intermediate the opposite ends of the channel. In some embodiments, the channel may be conical, cylindrical, or spherical, among others, optionally along a majority of the channel length.

A compliant member of compliant interface 62 may be positioned or positionable at least partially in channel 138. For example, the compliant member may be located in counterbore 142 and/or elsewhere along channel 138, such as in barrel portion 126 at one position or two or more spaced positions along the channel.

Fixation element 56 may be configured to be disposed partially in channel 138, such that the fixation element extends along at least a majority of the length of the channel and out the inner end of channel 138, through femoral neck 92 and into femoral head 90, for anchorage in the femoral head (see FIG. 2). The fixation element may bridge one or more femoral fractures 94. (The plate member, such as the mounting portion and/or the barrel portion, also may bridge one or more of the same or different fractures.)

Fixation element 56 may have a shaft 64 and a bone-securing portion 66 extending from the leading end of the shaft (see FIGS. 2 and 3). Shaft 64 may be configured to slide parallel to the shaft's long axis inside channel 138, optionally at various angular orientations of the shaft produced by deformation of compliant interface 62 (if present). The shaft may be shaped to prevent the fixation element from turning about the fixation element's long axis after the barrel portion has been placed around the shaft. For example, the shaft may have one or more flats 144, grooves, and/or ridges, among others, extending along the shaft that engage a corresponding or complementary region formed by a wall of channel 138 or an element disposed therein.

Bone-securing portion 66 may (or may not) be wider than shaft 64 of fixation element 56. The bone-securing portion may not (or may) be advanceable through channel 138, which may (or may not) require that the fixation element be installed in the proximal femur before a portion of shaft 64 of the fixation element is received in channel 138.

Fixation system 120 (or system 50) also may include a stiffening insert 146 for placement at least partially into an axial bore 148 of fixation element 56 to provide a core in the fixation element (see FIGS. 3 and 4). The stiffening insert may be described as stiffening element or a stiffening rod. Stiffening insert 146 may attach to the fixation element, such as via threaded engagement, among others. Accordingly, stiffening insert 146 may have an external thread 150 that mates with an internal thread 152 defined by fixation element 56 (or vice versa), such as in axial bore 148. The stiffening insert also may (or may not) have a smooth (nonthreaded) shaft region 154 extending from external thread 150 and opposite a head 156 of stiffening insert 146. Head 156 may define a driver engagement structure 158, such as socket, a slot, external facets, etc., to allow the stiffening insert to be turn with a driver, for threaded advancement into the fixation element.

Figure 4A:
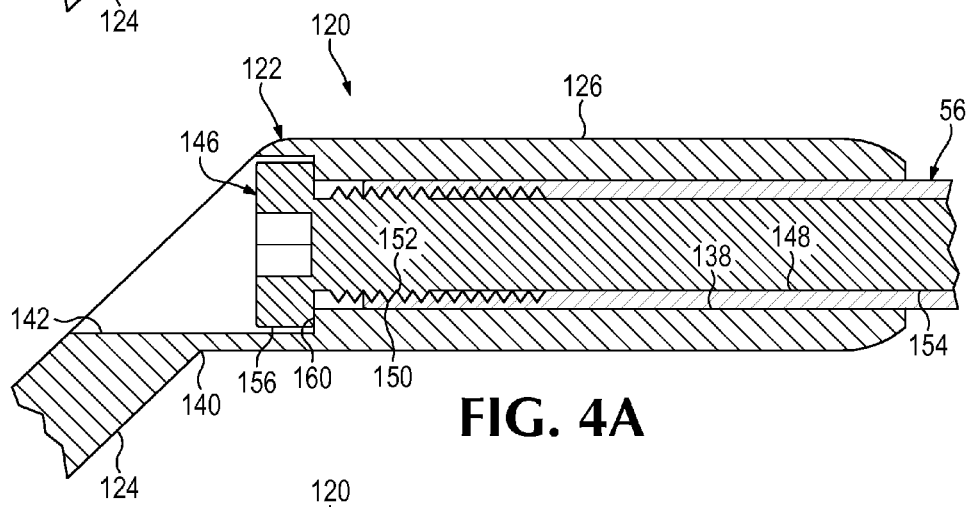
FIG. 4A is a fragmentary sectional view of a modified version of the plate-based system of FIG. 2, taken as in FIG. 4 but with a different stiffening insert having a wider head that allows the stiffening insert to also function as a compression screw, in accordance with aspects of the present disclosure.

Head 156 may have any suitable diameter. The head may or may not be larger in diameter than channel 138, to permit or restrict entry of the head into the main (narrower) part of the channel. FIG. 4 shows an embodiment of stiffening insert 146 where head 156 is small enough to pass through the channel. FIG. 4A shows an embodiment of stiffening insert 146 where head 156 is larger in diameter than the main part of the channel, such that head 156 is retained in counterbore 142. Accordingly, as shown in FIG. 4A, stiffening insert 146 can function as a compression screw when the stiffening insert is turned while head 156 is bearing against an end wall 160 of counterbore 142, which urges the fixation element 56 (and the attached femoral head) toward the counterbore.

Figure 4B:
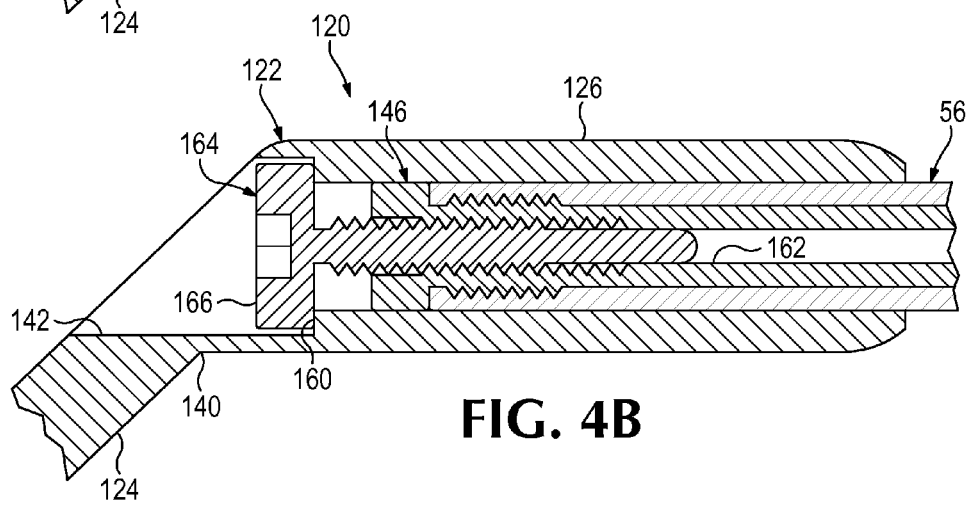
FIG. 4B is a fragmentary sectional view of another modified version of the plate-based system of FIG. 2, taken as in FIG. 4 but with a discrete compression screw extending into the stiffening insert, in accordance with aspects of the present disclosure.

FIG. 4B shows another modified version of fixation system 120. Here, stiffening insert 146 is sized to enter the main part of channel 138 and defines an internally threaded, axial bore 162. The system also has a discrete compression screw 164 with a head 166 that can bear against end wall 160 of counterbore 142. Accordingly, turning compression screw 164 can urge fixation element 56 and stiffening insert 146 as a unit toward counterbore 142, to apply adjustable compression to the proximal femur.

FIG. 5 shows further aspects of fixation element 56 of system 120, which also may be suitable for nail-based system 50 (optionally with modification to allow a bone-securing portion 66 of the fixation element to be advanced through the nail after placement of the nail into bone). Shaft 64 may define one or more openings 168, such as slits, that render the shaft flexible. For example, in the depicted embodiment, each opening 168 extends through the wall of shaft 64 to provide communication between axial bore 148 and the outside of the shaft. Openings 168 may be arranged along and around the shaft to render any suitable portion of the shaft flexible. For example, the openings may be arranged, sized, and shaped to provide axisymmetric flexibility, or flexibility that is not axisymmetric. Also, the openings may be configured to determine the flexion limit of the fixation element. The flexion limit may or may not be axisymmetric. In some embodiments, a series of openings 168 may be angularly offset from one another about the central long axis of the fastener, such as offset by about 60, 90, or 120 degrees, among others. In the depicted embodiment, successive openings are offset by 90 degrees from one another. In other embodiments, a single opening (e.g., a helical slit) may impart flexibility to the shaft (see Example 1 of Section V). The openings may be created by any suitable mechanism, such a cutting with a laser, electrical discharge machining, etching, a water jet, or the like. The openings may be positioned along any suitable longitudinal portion of shaft 64, such as less or more than one half of the shaft's length. In the depicted embodiments, the openings are defined only by a leading region of shaft 64, near bone-securing portion 66.

FIGS. 6-8 show fixation element 56 of FIG. 5 assembled with each insert (146a, 146b, or 146c) of an exemplary set of stiffening inserts configured to stiffen a compliant region of the fixation element differently from one another. Accordingly, the deformability (e.g., the flexibility) of fixation element 56 can be adjusted with appropriate selection of the insert.

Each insert may be placed into axial bore 148 to alter the flexibility of the fixation element, generally to increase the stiffness of the fixation element, and, optionally, to provide dampening. The insert may increase stiffness in an axisymmetric or non-axisymmetric manner. Either or both of the fixation element and the insert may be formed of polymer, metal, or a combination thereof (e.g., to provide optimal dampening). In exemplary embodiments, the fixation element is formed of metal and the insert is formed of metal or a polymer, such as an elastomer, or both metal and a polymer.

Stiffening inserts 146a-146c may have any suitable characteristics. The inserts may be of different length, diameter, flexibility per unit length, angle of taper, length of taper, composition, number and/or position of openings to increase insert flexibility, or any combination thereof, among others. Each insert may be tapered where the insert overlaps compliant region 68, to allow for a smoother load transmission between the fixation element and the insert. Each insert may attach to the fixation element by any suitable mechanism, such as a threaded connection, a friction fit, an adhesive, or the like. The insert may be configured to function as a compression screw (see FIG. 4A) or may permit attachment of a compression screw (see FIG. 4B).

The stiffening inserts may be configured to produce different effects on the flexibility of the fixation element. For example, each insert may overlap a different length of compliant region 68, to produce a different change in the flexibility of the fixation element. In the depicted embodiments, insert 146a extends through the entire flexible region and stiffens the fixation element the most (FIG. 6), while insert 146c overlaps less than one-half the length of flexible region and stiffens the fixation element the least (FIG. 8).

A suitable stiffening insert may be selected from a set of different stiffening inserts for placement into the fixation element. Selection may be based on one or more characteristics of the patient (i.e., the subject and implant recipient), such as according to the patient's weight, age, health, fitness level, activity level, or a combination thereof, among others.

FIGS. 8A and 8B show a modified version of fixation system 120 having an infinitely (continuously) adjustable flexibility. The system is depicted in the presence of a driver 170 that is operable to turn stiffening insert 146 for flexibility adjustment. Insert 146 may be sized to be advanceable completely into axial bore 148 of the fixation element, and internal thread 152 of fixation element 56 may extend farther into the fixation element than in FIGS. 4, 4A and 4B. Accordingly, insert 146 may be advanced a selectable extent by the surgeon, to produce a suitable overlap with compliant region 68 (e.g., as in FIGS. 6-8), thereby increasing the stiffness of the fixation element's compliant region 68 by an amount suitable for the subject. This adjustment also may be performed at a later time as needed after the installation of the system, for example, as the bone begins to heal and/or to improve performance and/or comfort.

Driver may have a shaft providing a depth gauge 172. The surgeon may compare indicia of the depth gauge with a reference mark 174 or other reference point of plate member 122, as insert 146 is being turned and advanced, to determine when a target depth (and thus a desired flexibility) has been reached.

Further aspects of nail-based system 50, plate-based system 120, compliant interface 62, and fixation element 56 for either system are described elsewhere herein, such as in Section V, and in the patent applications listed above under Cross-References to Priority Applications, which are incorporated herein by reference.

II. METHODS OF HIP FIXATION

This section describes exemplary methods of bone fixation using any of the systems disclosed herein. The method steps described in this section may be performed in any suitable order and combination and may be combined with any other steps or system features disclosed elsewhere herein.

A bone to be fixed may be selected. The bone may be a femur or a humerus, among others. The bone may have at least one discontinuity, such as at least one fracture. The discontinuity may be disposed in a proximal region of the bone. For example, the discontinuity may be disposed generally between the shaft and the head of the bone. In some embodiments, the bone may be a fractured proximal femur having at least one fracture intersecting the neck, intertrochanteric, and/or pertrochanteric region(s) of the proximal femur. Accordingly, the fracture(s) may intersect the femoral neck, the greater trochanter, the lesser trochanter, the shaft, or a combination thereof.

The bone may be prepared for receiving at least a portion of a fixation system. For example, one or more holes may be drilled in the bone to receive the deformable fixation element, the barrel portion of plate member, and/or fasteners, such as bone screws. Also, the medullary canal may be accessed and widened, if necessary, to receive a nail. Furthermore, pieces of the bone may be moved relative to another to reduce the fracture(s). One or more incisions through skin and other overlying soft tissue may be created to access the bone.

The bone-securing portion of a fixation element may be placed into the head of the bone. For example, the bone-securing portion may be driven into the head by application of torque (i.e., by turning the bone-securing portion), percussive force (e.g., striking a portion of the fixation element), or a combination thereof, among others. The bone-securing portion and the shaft of the fixation element may be placed into the bone as a unit, or at least part of the shaft may be placed into the bone after the bone-securing portion has been installed in bone.

A nail member may be selected for placement axially into the bone. Alternatively, a plate member may be selected for attachment to the bone and assembly with the deformable fixation element. The nail or plate member may be selected based on the size of the fixation element, the size and condition of the bone (e.g., the position and number of fractures or other discontinuities), and/or the like.

A portion of the deformable fixation element may be placed in an aperture of the nail or plate member. The deformable fixation element and the aperture may be arranged at least generally coaxial to one another, with the shaft extending out a medial side of the nail or from a barrel portion of the plate member. Placement of a portion of the deformable fixation element in the nail's or plate member's aperture may be performed before, during, and/or after a securing portion of the fixation element is placed into the head of the bone.

The nail or plate member may be attached to bone with one or more fasteners, such as bone screws. The nail or a mounting portion of the plate member may be arranged longitudinally in or on the bone.

The fixation element may be adjusted to urge the head of the bone at least generally toward the bone's shaft. Adjustment of the fixation element may include turning a compression screw that is attached to the fixation element.

In some embodiments, a stiffening insert may be placed at least partially into the fixation element. The stiffening insert may be selected from a set of different inserts that produce different effects on the deformability and/or flexibility of the fixation element. The insert may be placed into the fixation element before or after the fixation element is placed into bone.

The stiffening insert and/or a position thereof along a long axis defined by the fixation element may be selected based on a characteristic of the subject, such as weight, height, level of fitness, activity level, or a combination thereof, among other. Selection of a suitable stiffening insert or insert position may modulate load dampening in a subject-appropriate manner and/or may optimize the amount of micromotion at the fracture site(s) needed by the subject for efficient healing.

The incision(s) may be closed over the implant. The implant may be left in place permanently or may be removed after the bone has healed.

III. COMPOSITION OF SYSTEM COMPONENTS

This section describes exemplary materials for construction of components of the hip fixation system.

The nail, plate member, fixation element, fasteners, and compliant interface may be formed of any suitable biocompatible material(s). Exemplary biocompatible materials that may be suitable include (1) metal (for example, titanium or titanium alloys, alloys with cobalt and chromium (cobalt-chrome), stainless steel, etc.); (2) plastic/polymer (for example, ultra-high molecular weight polyethylene (UHM-WPE), thermoplastic polyurethane (TPU), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) composites (e.g., a polymer matrix (such as PEEK) containing carbon fibers and/or ceramic); (4) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, etc.; and/or the like.

In exemplary embodiments, the nail or plate member is formed of metal, and the fixation element is formed of metal (e.g., spring steel), polymer (e.g., an elastomer (such as thermoplastic polyurethane)), or a combination thereof.

IV. KITS

The fixation system may be provided as a system or kit with two or more different options for at least one of the components. For example, the system/kit may include two or more nails or plate members of different size and/or shape. Alternatively, or in addition, the system/kit may include two or more deformable fixation elements of different size (e.g., different lengths), shape (e.g., different diameters), and/or flexibility/deformability. Furthermore, the system/kit may include two or more interchangeable compliant members for a compliant interface between the nail or plate member and the fixation element. The interchangeable compliant members may have different deformability (e.g., different flexibility/stiffness, range of motion, relative deformability in a pair of orthogonal planes, etc.).

V. EXAMPLES

The following examples describe selected aspects and embodiments of the present disclosure including exemplary compliant hip fixation systems and methods of installing the systems to fix bone. The components, aspects, and features of the systems described in each of these examples may be combined with one another and with the systems described above, in any suitable combination. These examples are intended for illustration and should not limit the entire scope of the present disclosure.

Example 1

Fixation Elements with Flexible Shafts

This example describes exemplary fixation elements for the hip fixation systems of Section I, with each fixation element having a shaft with a compliant region forming only a longitudinal portion of the shaft; see FIGS. 9-11.

FIG. 9 shows a fixation element 56 defining an opening in the form of a sinuous helical slit 180 that forms a compliant region 68. The slit may provide communication between an axial bore and the exterior of the fixation element. Slit 180 may create interlocking features composed of tabs 182 located in complementary recesses 184, which permit flexion of the element's shaft and torque transmission through the shaft.

FIG. 10 shows another exemplary fixation element 56 for the systems of Section I. The element has a neck or waist 190 that forms a compliant region 68 of the fixation element. Neck may represent narrowing of shaft 64 that is axisymmetric, bilateral, or unilateral. In some embodiments one or more indentations 192 bounding the neck may be filled with a polymer, such as an elastomer, indicated at 194, to improve dampening and/or provide a uniform diameter for shaft 64.

FIG. 11 shows an exemplary fixation element 56 having a compliant region 68 formed of a relatively more compliant material 200 of different composition than other longitudinal regions of the fixation element.

Example 2

Fixation Elements with a Flexible Bone-Securing Portion

This example describes exemplary fixation elements for the hip fixation systems of Section I, with each fixation element having a flexible bone-securing portion formed at a leading end region of the element; see FIGS. 12-20.

FIGS. 12-14 show a fixation element 56 with a bone-securing portion 66 having a compliant region 68 produced by a flexible blade 220. The blade extends from shaft 64 and may (or may not) be wider than the shaft to form a paddle-shaped element. The blade has a body 222 and a row of teeth 224 projecting from a center line of the body, with the row arranged parallel to the long axis of the fixation element. The size of gaps 226 between the teeth may determine how far the blade can be flexed downward (or upward); contact between the teeth, produced by flexing the blade, may establish a limit of downward flexion. Blade 220 may be configured to deform substantially in one plane of a set of three mutually orthogonal planes. In the depicted embodiment, the one plane is orthogonal to the axis along which FIG. 12 is viewed. Blade also may be configured to deform at least predominantly downward, shown in phantom at 228 in FIG. 12, relative to upward in the one plane. In some embodiments, the blade may have a helical shape.

FIGS. 15-17 show another exemplary fixation element 56 having a flexible bone-securing portion 66. The fixation element and particularly a shaft 64 thereof may or may not be disposed in a coaxial tube that extends through and/or forms part of the support member (i.e., the nail or plate member). Bone-securing portion 66 may be located outside the tube. The fixation element may include a flange or blade portion 240 and a longitudinal rib 242 projecting orthogonally from a center line of the blade portion, to form a T-shape in cross-section (see FIG. 17). Rib 242 defines a plurality of openings in securing portion 66 to create a row of teeth 244. The teeth may contact one another as bone-securing portion 66 flexes in response to load 88, to limit the extent of deformation permitted.

FIGS. 18-20 show another exemplary fixation element 56 having a flexible bone-securing portion 66, and structured similarly to fixation element of FIGS. 15-17. Here, rib 242 is wider and more rounded in cross section (compare FIGS. 17 and 20). Also, teeth 244 are wider (compare FIGS. 15 and 18).

Example 3

Fixation Elements with Internal Compliant Region

Figure 21:
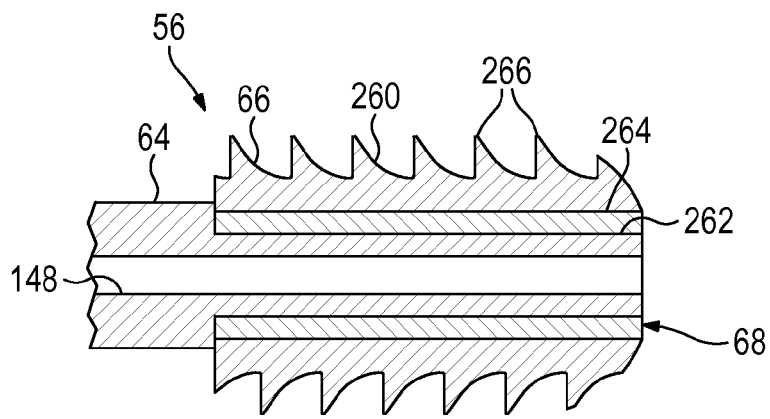
FIG. 21 is a fragmentary sectional view of another exemplary fixation element for the nail-based system of FIG. 1 or the plate-based system of FIG. 2, taken around a bone-securing portion of the fixation element that includes a core, a compliant member surrounding the core, and a threaded member mounted around the compliant member, in accordance with aspects of the present disclosure.
Figure 22:
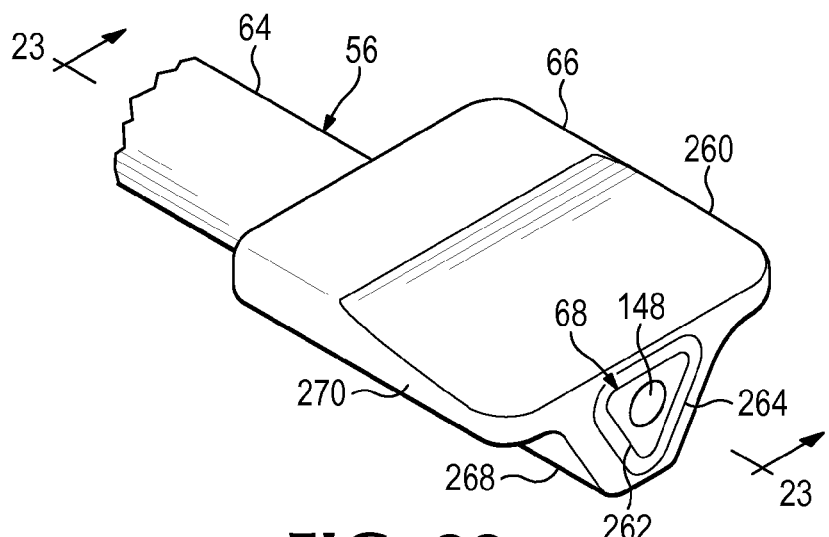
FIG. 22 is a fragmentary isometric view of still another exemplary fixation element for the nail-based system of FIG. 1 or the plate-based system of FIG. 2, taken around a bone-securing portion of the fixation element that includes a core, a compliant member surrounding the core, and a blade member mounted around the compliant member, in accordance with aspects of the present disclosure.
Figure 23:
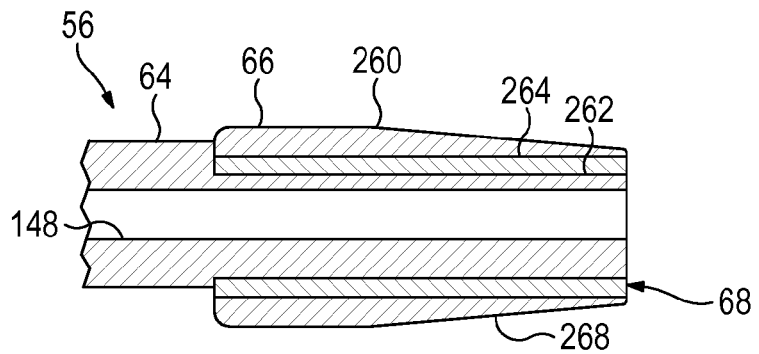
FIG. 23 is a fragmentary sectional view of the fixation element of FIG. 22, taken generally along line 23-23 of FIG. 22.

This example describes fixation elements 56 for the hip fixation systems of Section I, with each fixation element including a bone-securing portion 66 having an internal compliant region; see FIGS. 21-23.

FIG. 21 shows an exemplary three-part fixation element 56 having a shaft 64 and a compliant bone-securing portion 66. The bone-securing portion has a bone-engaging region 260 surrounded by a core 262, and separated from the core by a reversibly deformable compliant member 264 that forms compliant region 68 of the fixation element. Shaft 64 may or may not be formed integrally with core 262. Compliant member 264 may surround core 262 and may be structured as a layer (e.g., a tubular layer) disposed between core 262 and bone-engaging region 260. The bone-engaging region may have any suitable structure for anchoring the fixation element in bone, such as an external thread 266, barbs, a blade, teeth, etc. Bone-engaging region 260 may or may not be formed integrally with shaft 64 and/or core 262. Compliant member 264 may, for example, be formed of polymer, such as an elastomer, and the rest of the fixation element may, for example, be formed of metal. The compliant member may be molded around core 262, such as in situ between bone-engaging region 260 and core 262, or may be formed separately and the placed around the core. The space formed radially between the outside of the core and the inside of the bone-engaging region may be only partially or completely filled with the compliant member.

FIGS. 22 and 23 show another exemplary fixation element 56 having a compliant bone-securing portion 66. The fixation element is paddle-shaped but otherwise is similar to fixation element 56 of FIG. 21, and may have any of the elements and features described above. Accordingly, the fixation element has a shaft 64, a bone-engaging region 260, which may or may not be integral with shaft 64, a triangular core 262, and a compliant member 264. Bone-engaging region 260 may have a body 268 and a flange or blade 270 projecting from opposite sides of the body.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of hip fixation, the method comprising, in any order:
　　disposing a fixation element in a proximal femur and anchored to a head of the proximal femur, wherein the fixation element includes a compliant region that is reversibly deformable;
　　disposing a portion of the fixation element in an aperture of a support member including an intramedullary nail or a plate member, such that the fixation element is slideable in the aperture parallel to a long axis of the fixation element;
　　securing the support member to the femur; and
　　inserting a stiffening insert at least partially into the fixation element to reduce a deformability of the compliant region.

2. The method of claim 1, further comprising a step of selecting the stiffening insert from a set of stiffening inserts each configured to reduce the deformability differently from one another.

3. The method of claim 2, wherein the step of selecting the stiffening insert is based on one or more characteristics of a subject receiving the fixation element and the support member.

4. The method of claim 1, wherein the fixation element defines an axial channel, and wherein the stiffening insert is insertable completely into the axial channel to an adjustable depth such that the deformability of the compliant region is infinitely adjustable.

5. The method of claim 4, further comprising a step of measuring a depth of the stiffening insert or a characteristic corresponding to the depth.

\* \* \* \* \*